(12) United States Patent
Gon

(10) Patent No.: US 11,458,031 B2
(45) Date of Patent: Oct. 4, 2022

(54) STENT DELIVERY DEVICE

(71) Applicant: ZEON CORPORATION, Tokyo (JP)

(72) Inventor: Chimyon Gon, Tokyo (JP)

(73) Assignee: Zeon Corporation, Tokyo (JP)

( * ) Notice: Subject to any disclaimer, the term of this patent is extended or adjusted under 35 U.S.C. 154(b) by 90 days.

(21) Appl. No.: 16/496,395

(22) PCT Filed: Mar. 27, 2018

(86) PCT No.: PCT/JP2018/012453
§ 371 (c)(1),
(2) Date: Sep. 20, 2019

(87) PCT Pub. No.: WO2018/181326
PCT Pub. Date: Oct. 4, 2018

(65) Prior Publication Data
US 2021/0106448 A1 Apr. 15, 2021

(30) Foreign Application Priority Data
Mar. 31, 2017 (JP) .............................. JP2017-072834

(51) Int. Cl.
*A61F 2/966* (2013.01)
*A61B 17/34* (2006.01)
(Continued)

(52) U.S. Cl.
CPC .......... *A61F 2/966* (2013.01); *A61B 17/3417* (2013.01); *A61B 18/14* (2013.01);
(Continued)

(58) Field of Classification Search
CPC .............. A61F 2/966; A61F 2250/0029; A61F 2250/0037; A61B 18/14;
(Continued)

(56) References Cited

U.S. PATENT DOCUMENTS 5,238,005 A * 8/1993 Imran ............... A61M 25/0144
600/585
2002/0045929 A1 * 4/2002 Diaz ...................... A61F 2/966
623/1.11
(Continued)

FOREIGN PATENT DOCUMENTS

CN 105916457 A 8/2016
JP 3-505825 A 12/1991
(Continued)

OTHER PUBLICATIONS

Extended European Search Report, dated Nov. 13, 2020, issued in European Application No. EP 18776684.5.
(Continued)

*Primary Examiner* — Richard G Louis
(74) *Attorney, Agent, or Firm* — Knobbe, Martens, Olson & Bear, LLP

(57) ABSTRACT

Provided is a stent delivery device that can rapidly transport a stent to an indwelling site. In one aspect, the stent delivery device includes a catheter including an inner sheath and an outer sheath allowing the inner sheath to be slidably inserted therethrough and a stent provided between the inner sheath and the outer sheath in the vicinity of a distal end of the catheter. The stent delivery device also includes a guiding elongated body inserted through an inner lumen of the inner sheath and partially exposed from the distal end of the catheter so as to guide the insertion of the catheter. The guiding elongated body has a variable tip area provided in the vicinity of a distal end of the guiding elongated body so as to change flexibility between a first state and a second state different from the first state.

10 Claims, 9 Drawing Sheets

(51) Int. Cl.
  *A61B 17/00* (2006.01)
  *A61B 18/14* (2006.01)
(52) U.S. Cl.
  CPC ............... *A61B 2017/00292* (2013.01); *A61B 2017/00336* (2013.01); *A61B 2017/00353* (2013.01); *A61F 2250/0029* (2013.01)
(58) Field of Classification Search
  CPC ........... A61B 2017/00353; A61B 2017/00292; A61B 2017/00336; A61B 17/3417
  See application file for complete search history.

(56) References Cited

U.S. PATENT DOCUMENTS

| | | | |
|---|---|---|---|
| 2003/0139689 A1* | 7/2003 | Shturman | A61M 25/0141 600/585 |
| 2003/0171642 A1* | 9/2003 | Schock | A61M 25/09 600/18 |
| 2007/0149951 A1 | 6/2007 | Wu et al. | |
| 2007/0167804 A1* | 7/2007 | Park | A61B 8/12 600/459 |
| 2009/0264988 A1 | 10/2009 | Mafi et al. | |
| 2013/0131643 A1* | 5/2013 | Parodi | A61B 17/1214 604/528 |
| 2016/0158044 A1 | 6/2016 | Chou et al. | |

FOREIGN PATENT DOCUMENTS

| | | |
|---|---|---|
| JP | 2007-190376 A | 8/2007 |
| JP | 2010-524631 A | 7/2010 |
| JP | 2014-195556 A | 10/2014 |
| JP | 2016-189839 A | 11/2016 |
| WO | WO 1989/006985 A1 | 8/1989 |
| WO | WO 2008/133808 A1 | 11/2008 |
| WO | WO 2015/108941 A1 | 7/2015 |
| WO | WO 2017/027161 A1 | 2/2017 |

OTHER PUBLICATIONS

International Preliminary Report on Patentability in PCT/JP2018/012453 dated Oct. 10, 2019.
Office Action dated Jan. 6, 2021, corresponding to Chinese Patent Application No. 201880015596.9.
International Search Report in International Patent Application No. PCT/JP2018/012453 dated Jul. 3, 2018.

* cited by examiner

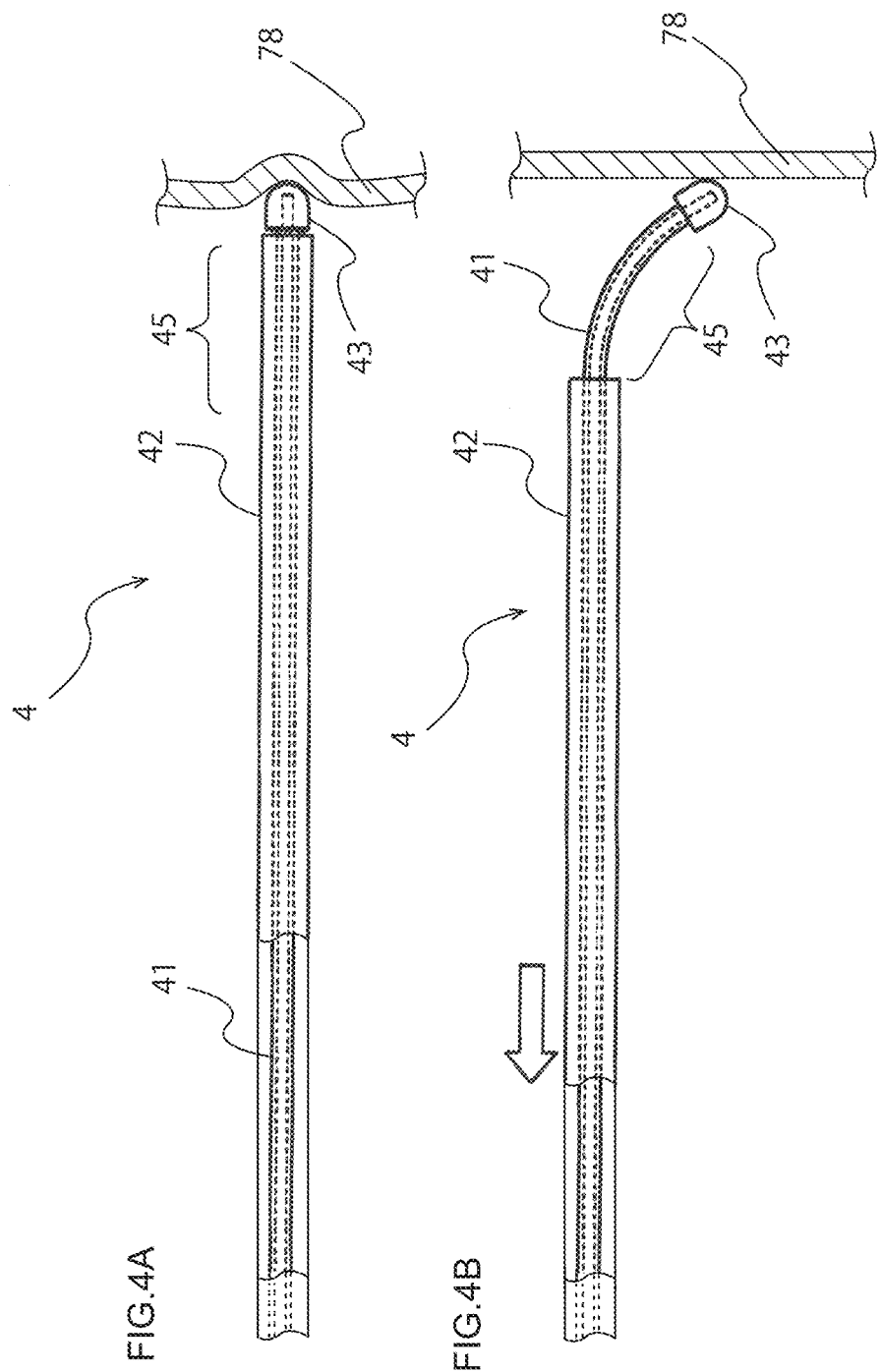

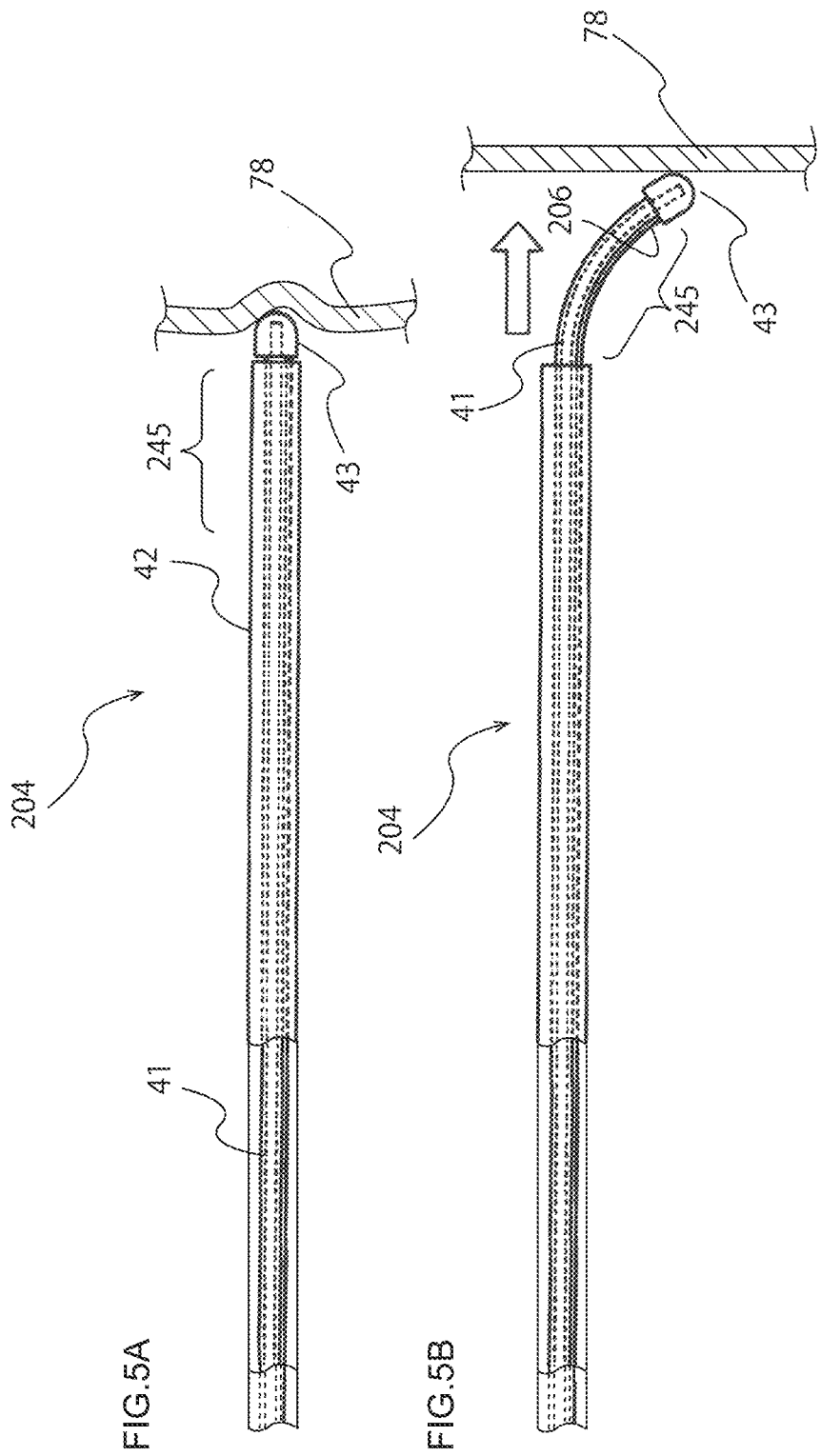

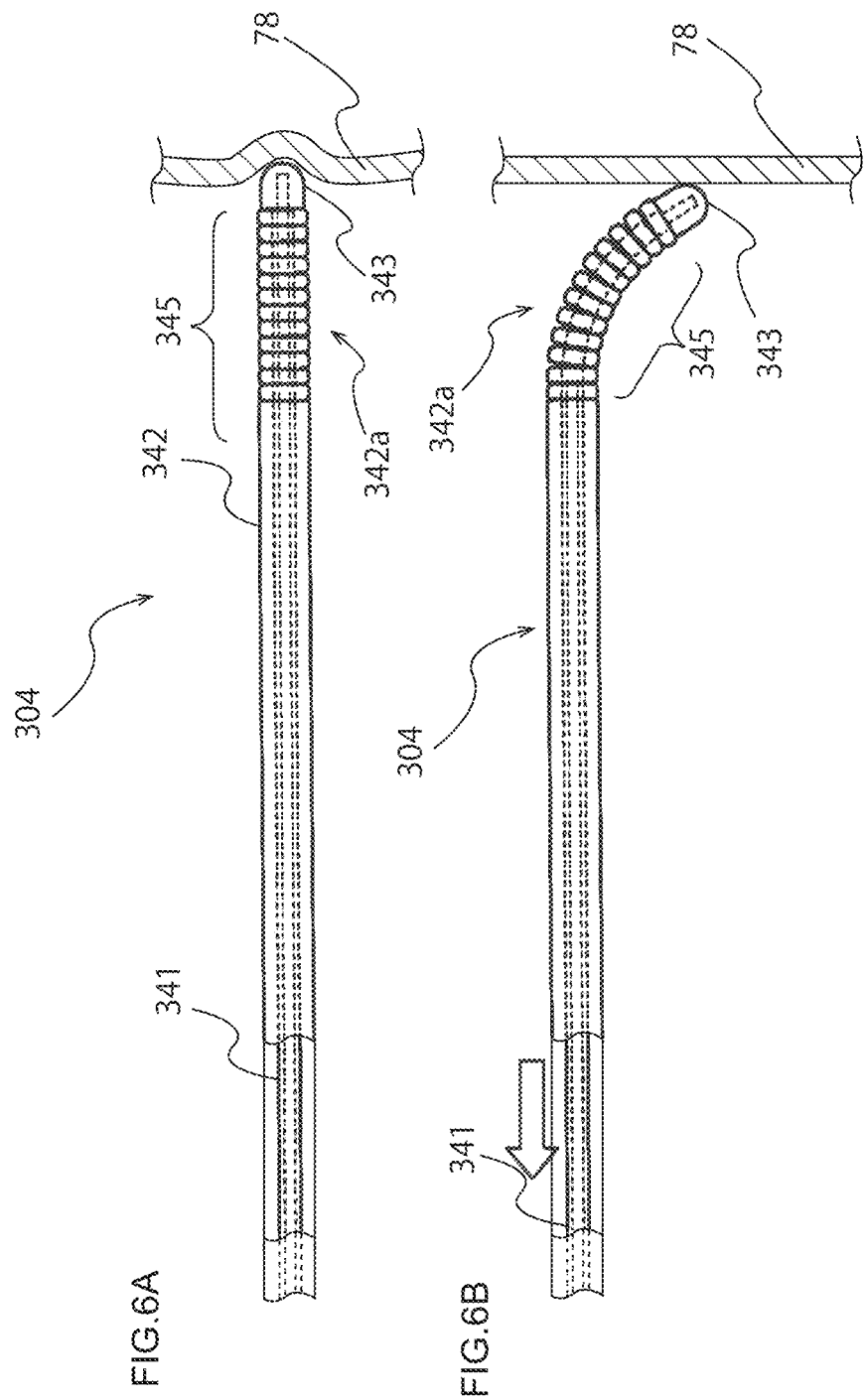

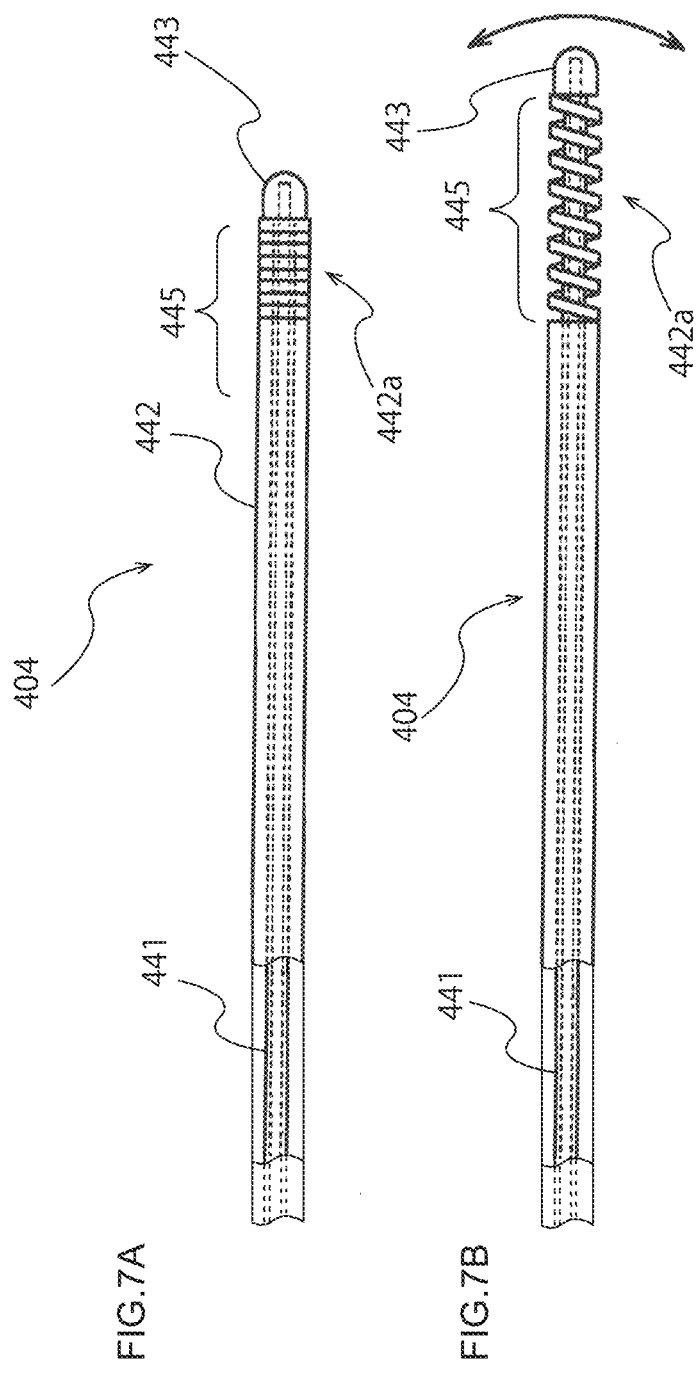

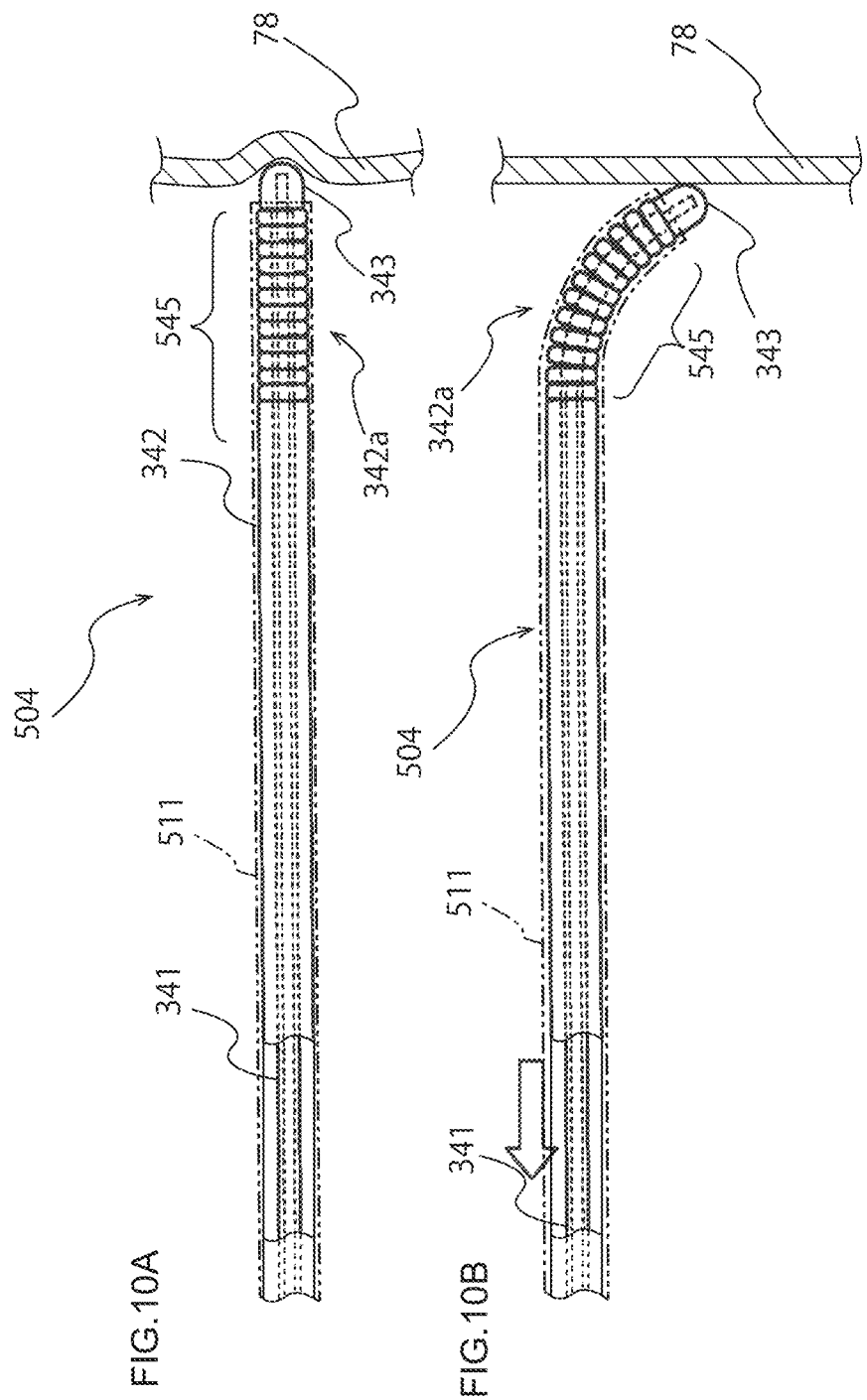

STENT DELIVERY DEVICE

TECHNICAL FIELD

The present invention relates to a stent delivery device which transports a stent to an indwelling site in a body and indwells the stent at that site.

BACKGROUND ART

In recent years, there have been sporadic cases of reports of endoscopic ultrasound-guided transduodenal (or transgastric transhepatic) biliary drainage (EUS-BD) when transduodenal papillary approaches are not available in the case of unresectable malignant biliary stricture or obstruction that requires biliary drainage. The EUS-BD is a procedure in which an ultrasound endoscope is inserted into a duodenum (or stomach), a common bile duct (or intrahepatic bile duct) is punctured by a puncture needle from a duodenum (or stomach) wall while observing an ultrasound image in real time, a guide wire is inserted into the bile duct through the punctured hole, and a tubular object corresponding to a bypass route connecting the duodenum (or stomach) and the common bile duct (or intrahepatic bile duct) is inserted and indwelled along the guide wire. By this procedure, biliary drainage can be achieved by implanting the tubular object into the body.

A self-expanding stent provided with a covering film may be used as the tubular object used as the bypass route in such EUS-BD. As a stent delivery device used in this case, for example, one including a catheter with an inner sheath and an outer sheath allowing the inner sheath to be slidably inserted therethrough is known. Here, a stent is disposed in a stent placement portion provided in the vicinity of a distal end of the inner sheath and the stent is held in a contracted state inside the vicinity of the distal end of the outer sheath. Further, when the outer sheath is slid to be pulled out from the inner sheath at the proximal end side of the catheter, the stent is expanded.

For example, when the stomach is bypass-connected to the intrahepatic bile duct, the puncture needle forms a hole from the stomach wall through an abdominal cavity to the intrahepatic bile duct and the guide wire is inserted to secure the route. Then, the punctured hole is expanded by a dilator to a degree that the distal end portion of the catheter is inserted thereinto and the distal end portion of the catheter (the stent placement portion) is inserted through the punctured hole. Subsequently, when the outer sheath is pulled out in this state and the stent is released (exposed and expanded), the stent is indwelled in the punctured hole.

In the EUS-BD, since such a complex procedure is performed, a stent delivery device capable of rapidly transporting a stent is required. For example, Patent Document 1 proposes a catheter of which a distal side is provided with a distal end tip having a high modulus material on the distal side and a low modulus material on the proximal side. As a result, since the distal end tip has high piercing ability (pushability) and flexibility, the catheter can be inserted smoothly without damaging a body lumen.

CITATION LIST

Patent Document

Patent Document 1: JP 2014-195556 A

SUMMARY OF THE INVENTION

Problem to be Solved by the Invention

The invention has been made in view of such circumstances and an object of the invention is to provide a stent delivery device capable of rapidly delivering a stent to an indwelling site.

Means for Solving Problem

In order to attain the above-described object, a stent delivery device according to the invention includes: a catheter which includes an inner sheath and an outer sheath allowing the inner sheath to be slidably inserted therethrough; a stent which is provided between the inner sheath and the outer sheath in the vicinity of a distal end of the catheter; and a guiding elongated body which is inserted through an inner lumen of the inner sheath and is capable of partially exposed from the distal end of the catheter so as to guide the insertion of the catheter, in which the guiding elongated body has a variable tip area provided in the vicinity of a distal end of the guiding elongated body, and the variable tip area has an ability of changing flexibility between a first state in which the variable tip area has predetermined flexibility and a second state in which the variable tip area is stiffer than the first state.

Since the stent delivery device according to the invention includes the guiding elongated body with the variable tip area capable of changing the flexibility, the stent provided in the vicinity of the distal end of the catheter can be rapidly transported to the indwelling site and be indwelled at that site by changing the flexibility of the guiding elongated body depending on the procedure and the patient's internal body condition.

Further, for example, the guiding elongated body may include a puncturing portion which is provided in the distal end of the guiding elongated body so as to puncture a wall of an organ.

In such a stent delivery device, since the puncturing portion can be strongly pressed against the corresponding site by setting the variable tip area of the guiding elongated body to the second state, the puncturing can be rapidly performed. Further, if the variable tip area of the guiding elongated body is set to the first state when the puncturing is not performed, it is possible to prevent the puncturing portion from being strongly pressed against a wall of an organ. Further, since the guiding elongated body has a function of a puncturing tool and a function of guiding the catheter like the guide wire, it is possible to omit a replacement operation of a wire or the like inserted through an inner lumen and to rapidly transport the stent to the indwelling site.

For example, the puncturing portion may include an electrode for cauterizing a wall of an organ.

Since the puncturing portion having such an electrode does not need to have a sharp tip due to the needle of the puncturing portion, such a guiding elongated body can prevent a site other than the punctured site from being damaged by the puncturing portion. Further, since such a guiding elongated body is used, it is possible to more rapidly perform a procedure and to transport a stent to the indwelling site.

The guiding elongated body may include an inner elongated body and an outer tube through which the inner elongated body is slidably inserted.

Such a guiding elongated body can easily change the variable tip area state between the first state and the second state by sliding the inner elongated body and the outer tube.

Further, for example, when the variable tip area is in the first state, an exposure length in which the inner elongated body is exposed from a distal end of the outer tube may be a first length, and when the variable tip area is in the second state, the exposure length may be a second length shorter than the first length.

Such a guiding elongated body can rapidly and easily change the first state and the second state, for example, in such a manner that the inner elongated body is exposed from the outer tube so that the variable tip area becomes the first state and the inner elongated body is accommodated in the outer tube so that the variable tip area becomes the second state.

Further, for example, when the variable tip area is in the first state, a non-overlapping length in which the outer tube and the inner elongated body do not overlap each other in the vicinity of the distal end of the guiding elongated body may be a third length, and when the variable tip area is in the second state, the non-overlapping length may be a fourth length shorter than the third length.

Such a guiding elongated body can rapidly and easily change the first state and the second state from the proximal end side of the guiding elongated body, for example, in such a manner that the distal end of the inner elongated body is pulled to the proximal end side of the outer tube so that the variable tip area becomes the first state and the distal end of the inner elongated body is pushed to the distal end side of the outer tube so that the variable tip area becomes the second state.

Further, for example, the outer tube may include a telescopic distal end portion which is provided in the vicinity of a distal end of the outer tube and having elasticity in an axial direction while changing the flexibility.

Such a guiding elongated body including the outer tube can rapidly and easily change the first state and the second state of the variable tip area from the proximal end side of the guiding elongated body, for example, in such a manner that the proximal end of the outer tube is moved to the proximal end side to expand the telescopic distal end portion so that the variable tip area becomes the first state and the proximal end of the outer tube is moved to the distal end side to contract the telescopic distal end portion so that the variable tip area becomes the second state.

Further, the stent delivery device of the invention may further include an operation wire which is connected to the distal end of the guiding elongated body and inserted through the inner lumen of the inner sheath in parallel to the guiding elongated body, wherein the operation wire is used to operate bending and stretching in the vicinity of the distal end of the guiding elongated body.

Such a stent delivery device including the operation wire can rapidly perform a procedure and rapidly transport the stent to the indwelling site by allowing an operator to operate the bending and stretching of the distal end portion of the guiding elongated body.

BRIEF DESCRIPTION OF DRAWINGS

FIG. 4A is a side view illustrating a second state of a variable tip area of the guiding elongated body of the stent delivery device illustrated in FIG. 1 and FIG. 4B is a side view illustrating a first state of the variable tip area;

FIG. 5A is a side view illustrating a second state of a variable tip area of a guiding elongated body of a stent delivery device according to a second embodiment of the invention and FIG. 5B is a side view illustrating a first state of the variable tip area;

FIG. 6A is a side view illustrating a second state of a variable tip area of a guiding elongated body of a stent delivery device according to a third embodiment of the invention and FIG. 6B is a side view illustrating a first state of the variable tip area;

FIG. 7A is a side view illustrating a second state of a variable tip area of a guiding elongated body of a stent delivery device according to a fourth embodiment of the invention and FIG. 7B is a side view illustrating a first state of the variable tip area;

FIG. 10A is a side view illustrating a second state of a variable tip area of a guiding elongated body of a stent delivery device according to a second modified example of the invention and FIG. 10B is a side view illustrating a first state of the variable tip area.

MODE(S) FOR CARRYING OUT THE INVENTION

First Embodiment

Hereinafter, an embodiment of the invention will be described in detail with reference to the drawings. In the embodiment, an exemplary case in which an ultrasonic endoscope-guided transgastric transhepatic biliary drainage (EUS-BD), that is, a self-expanding stent provided with a covering film for bypass-connecting a stomach and an intrahepatic bile duct is indwelled and another stent is indwelled in the bile duct will be described. However, the stent delivery device according to the invention is not limited to one that bypass-connects the stomach and the intrahepatic bile duct and can be widely applied to those which bypass-connect luminal organs and other luminal organs such as duodenum and common bile duct. Further, the stent delivery device according to the invention is not limited to the case of indwelling a stent for bypass-connection and can be also applied to a transduodenal papillary biliary drainage (for indwelling a stent at a stenosis in the common bile duct) and one for indwelling a stent at a stenosis in a lumen other than the common bile duct.

Figure 1:
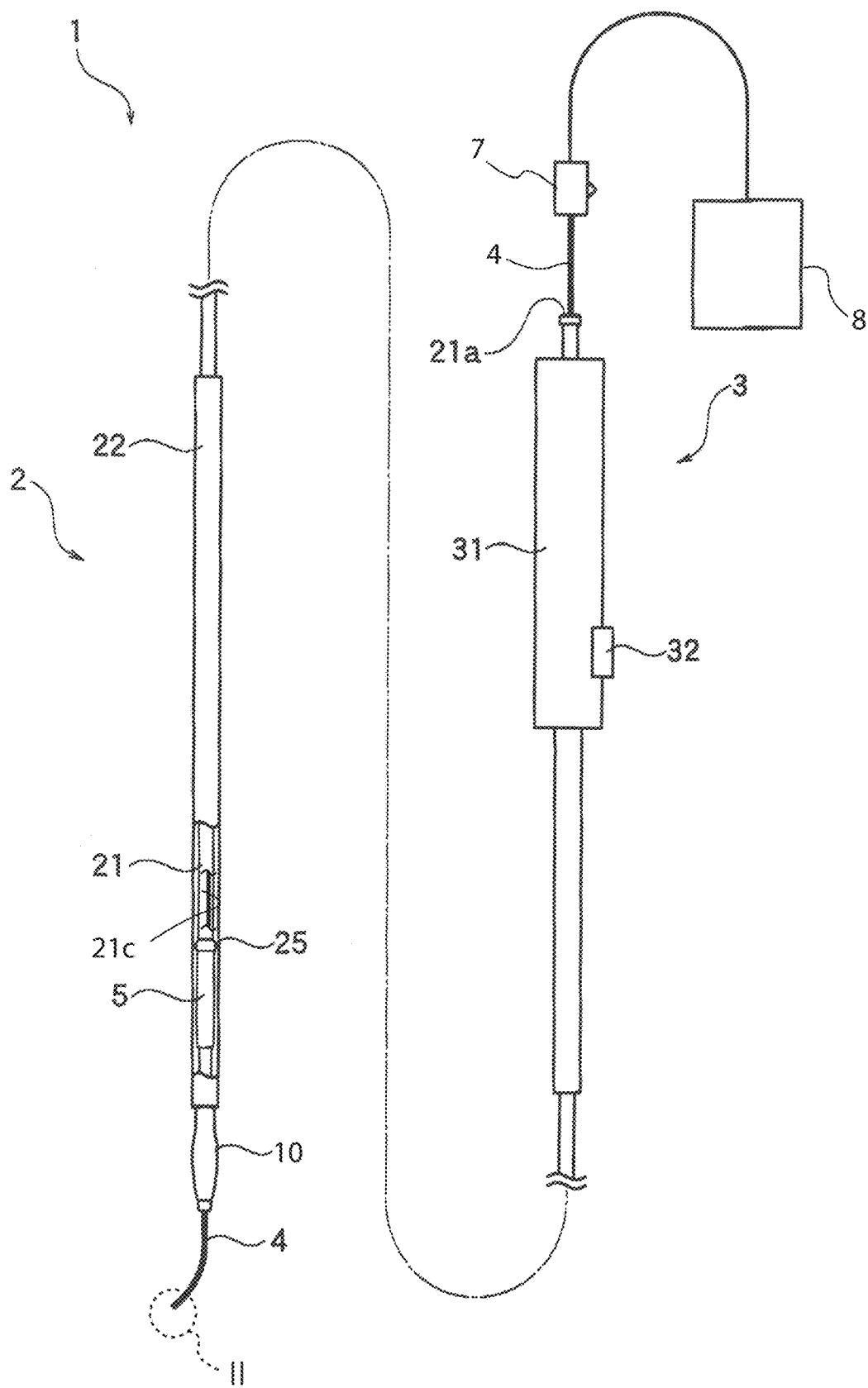
FIG. 1 is a schematic diagram illustrating an overall configuration of a stent delivery device according to a first embodiment of the invention.

As illustrated in FIG. 1, a stent delivery device 1 schematically includes an elongated catheter 2 which is inserted into a patient's body (lumen) through a treatment instrument guide tube of an endoscope (not illustrated), an operation unit 3 which is connected to a proximal end side of the catheter 2 and operates the catheter 2 inside a body from the outside of the body, a guiding elongated body 4, a stent 5 which is an indwelling target, and a distal end tip 10. Although the vicinity of the distal end of the catheter 2 including the stent 5 may be curved depending on the shape of the site to be indwelled, it is drawn linearly for convenience of the drawing.

The catheter 2 includes an inner sheath 21 which includes a distal end and a proximal end and an outer sheath 22 which includes a distal end and a proximal end. As illustrated in FIG. 1, the inner sheath 21 is inserted through the lumen of the outer sheath 22 so as to be slidable.

A contrast marker (not illustrated) is attached to the vicinity of the distal ends of the inner sheath 21 and the outer sheath 22. The contrast marker is a marker of which a position is detected by X-ray fluoroscopy and becomes a marker in the body. For example, the contrast marker is formed of a metal material such as gold, platinum, and tungsten or a polymer blended with barium sulfate or bismuth oxide.

The inner sheath 21 is formed as an elongated tube having flexibility and the guiding elongated body 4 serving as a guide for inserting the catheter 2 into a patient's body is inserted through an inner lumen 21c which is a lumen thereof. The distal end of the catheter 2 can be inserted into a target site inside the body as the catheter 2 is pushed (moved forward) along the guiding elongated body 4 after the guiding elongated body 4 is inserted into the body to secure a path inside and outside the body. The outer diameter of the inner sheath 21 (a portion for disposing the stent 5 to be described later) is about 0.5 to 3.5 mm.

As illustrated in FIG. 4, the guiding elongated body 4 includes a variable tip area 45 and has another function of puncturing a wall of an organ as well as a function of guiding the catheter 2 as in a normal guide wire. The variable tip area 45 and other functions of the guiding elongated body 4 will be described later. Additionally, the catheter 2 may be inserted into the inner lumen 21c by exchanging a guide wire, a dilator, or another tube with the guiding elongated body 4.

As illustrated in FIG. 1, a fixing ring 25 is integrally fixed to the vicinity of the distal end of the inner sheath 21. The fixing ring 25 is used to define the position of the proximal end of the stent 5 and a gap between the inner sheath 21 and the outer sheath 22 in a portion from the fixing ring 25 to the distal end becomes a stent placement portion. The stent 5 is disposed in the stent placement portion. Further, a proximal end side portion in relation to the fixing ring 25 in the inner sheath 21 is provided with another elongated tube (not illustrated) coaxially provided to cover an elongated tube constituting a body of the inner sheath 21 and a proximal end side portion in relation to the fixing ring 25 in the inner sheath 21 is thicker than a distal end side portion in relation to the fixing ring 25 in the inner sheath 21. In this way, since the proximal end side portion in relation to the fixing ring 25 in the inner sheath 21 is thick, the pushability of the inner sheath 21 increases. Accordingly, the operability becomes satisfactory and the deviation of the position of the fixing ring 25 toward the proximal end side is prevented.

The outer sheath 22 is formed as an elongated tube having flexibility and has an inner diameter slightly larger than the outer diameter of the inner sheath 21. The inner sheath 21 is slidably inserted into the outer sheath. The inner diameter of the outer sheath 22 is about 0.5 to 3.5 mm and the outer diameter thereof is about 1.0 to 4.0 mm. The outer sheath 22 is slidable (relatively movable) in the axial direction with respect to the inner sheath 21 in such a manner that the operation unit 3 connected to the proximal ends of the outer sheath 22 and the inner sheath 21 is operated by an operator.

As the materials of the inner sheath 21 and the outer sheath 22, for example, various resin materials including polyolefins such as polyethylene and polypropylene, polyvinyl chloride, polyurethane, ethylene-vinyl acetate copolymer, polyester such as polyethylene terephthalate and polybutylene terephthalate, polyamide, polyether polyamide, polyester polyamide, polyether ether ketone, polyether imide and fluorine-based resins such as polytetrafluoroethylene and tetrafluoroethylene/hexafluoropropylene copolymer, or various thermoplastic elastomers such as polystyrene based elastomers, polyolefin based elastomers, polyurethane based elastomers, polyester based elastomers, polyamide based elastomers, and polybutadiene based elastomers can be used. Two or more of these can be used in combination. Further, the inner sheath 21 and the outer sheath 22 may be respectively provided with reinforcing materials formed in a blade shape or a coil shape by a wire formed of metal such as stainless steel or tungsten or high-rigidity resin such as liquid crystal polymer.

Additionally, although it is not provided in the embodiment, an outermost tube (not illustrated) may be coaxially disposed on the outside of the outer sheath 22. The outermost tube is formed as an elongated tube having flexibility and includes a lumen into which the outer sheath 22 is slidably inserted. As the outermost tube, one having a size larger than the outer diameter of the outer sheath 22 by about 0.05 to 1.0 mm can be used. As the material of the outermost tube, polyacetal, polytetrafluoroethylene, tetrafluoroethylene/hexafluoropropylene copolymer, polypropylene, or the like can be used.

The stent 5 is a self-expanding stent which expands from its contracted state by its own elastic force and has a cylindrical bare stent formed by a frame. A covered stent is used as a stent for bypass-connection between organs and in addition to a bare stent, a covered stent has a covering film portion that covers the outer periphery of the bare stent. The bare stent is formed of super elastic metal such as nickel titanium alloy, cobalt chromium alloy, gold titanium alloy, beta titanium alloy, or shape memory metal. In the case of the covered stent, the surface of the bare stent is covered with a coating that extends to fill between adjacent frames and the outer periphery of the bare stent covered with the coating is covered by a covering film such as a polymer film.

Although the total length of the stent 5 is determined depending on the application such as the distance between the lumen organs to be bypass-connected, the total length is about 30 to 200 mm. Further, although the outer diameter in an expanded state is determined depending on the type and size of the luminal organ to be bypass-connected, the size of the lumen in which the stent 5 is indwelled, and the like, the outer diameter is about $\phi 2$ to $\phi 20$ mm. The outer diameter of the stent 5 in a contracted state is about a fraction of the outer diameter in the expanded state. Additionally, in the embodiment, the stent 5 is described as one component of the stent delivery device 1, but the stent 5 can be replaced as a member separated from the stent delivery device 1.

The operation unit 3 connected to the proximal end of the stent 5 includes a substantially cylindrical release handle (housing) 31, a distal end lid member having a penetration hole formed at the center portion is integrally attached to the distal end side opening of the release handle 31 so as to close the opening, and a proximal end lid member having a penetration hole formed at the center portion thereof is integrally attached to the proximal end side opening so as to close the opening.

The proximal end of the outer sheath 22 is slidably inserted through the penetration hole of the distal end lid member of the release handle 31 and the proximal end of the outer sheath 22 is located inside the release handle 31.

Further, the operation unit 3 includes a release lever 32 which slidably engages with the release handle 31. The release lever 32 includes a head portion which is located outside the release handle 31 and a foot portion which is formed uprightly at the center portion of the head portion and is located inside the release handle 31.

The front end (the lower end) of the foot portion of the release lever 32 is fixed to the proximal end of the outer sheath 22 located inside the release handle 31. When the release lever 32 is slid, the outer sheath 22 can be slid to the proximal end side or the distal end side with respect to the inner sheath 21 fixed to the release handle 31 (the proximal end lid member).

The proximal end of the inner sheath 21 inserted through the outer sheath 22 passes through the release handle 31 and penetrates the penetration hole of the proximal end lid member of the release handle 31 so that its proximal end is located outside the release handle 31. The inner sheath 21 is fixed to the proximal end lid member (the release handle 31) at the penetration hole portion.

In a state in which the release lever 32 is moved to the distal end side, as illustrated in FIG. 1, the distal end of the outer sheath 22 reaches the distal end tip 10. Accordingly, in the stent delivery device 1, the stent 5 is held inside the outer sheath 22 while being contracted at the stent placement portion of the inner sheath 21. When the release lever 32 is moved to the proximal end side of the groove from this state, the outer sheath 22 is slid to the proximal end side with respect to the inner sheath 21 so that the stent 5 is relatively pushed out from the distal end of the outer sheath 22 and the stent 5 is released (expanded) by the self-expanding force.

The distal end tip 10 is attached to the distal end portion of the inner sheath 21. When the distal end of the inner sheath 21 (the catheter 2) collides with the peripheral wall of the body lumen, the distal end tip 10 reduces the stimulation on the body lumen and further reduces the insertion resistance of the catheter 2 so that the insertion into the body is facilitated. The distal end tip 10 is formed of, for example, a resin such as polyethylene (PE), polyamide (PA), or polyurethane (PU).

The distal end tip 10 is provided with a penetration hole communicating with the inner lumen 21c of the inner sheath 21 and a part (a part in the vicinity of the distal end) of the guiding elongated body 4 inserted through the inner lumen 21c of the inner sheath 21 is exposed from the distal end of the catheter 2 through the penetration hole of the distal end tip 10.

The guiding elongated body 4 can be used as a guide for inserting the catheter 2 into the patient's body as illustrated in FIG. 1. The guiding elongated body 4 is inserted through the inner lumen 21c of the inner sheath 21 and is disposed so that its distal end protrudes from the opening of the distal end of the distal end tip 10 of the inner sheath 21 and its proximal end is exposed to the outside through a proximal end opening 21a of the inner sheath 21 disposed to penetrate the operation unit 3. The outer diameter of the guiding elongated body 4 can be set to about 0.025 inch (≈0.635 mm) to 0.035 inch (≈0.889 mm) similarly to the diameter of the general guide wire. However, the guiding elongated body 4 may have an outer diameter in which the inner sheath 21 can be inserted and may have an outer diameter different from the diameter of the general guide wire.

Figure 2:
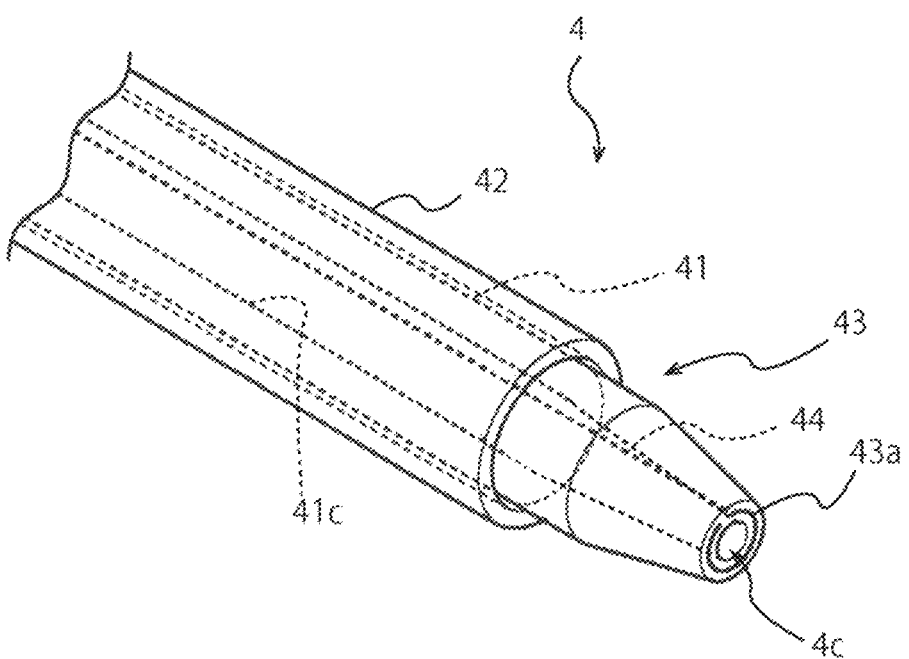
FIG. 2 is a perspective view illustrating a distal end portion of a guiding elongated body of the stent delivery device illustrated in FIG. 1.

FIG. 2 is a perspective view illustrating a distal end portion of the guiding elongated body 4 illustrated in FIG. 1. The guiding elongated body 4 has a double tube structure including an inner elongated body 41 which is a tubular body having an innermost lumen 41c formed therein and an outer tube 42 through which the inner elongated body 41 is slidably inserted. Further, an elongated body distal end tip 43 is provided at the distal end of the guiding elongated body 4.

The elongated body distal end tip 43 includes an electrode 43a cauterizing a wall of an organ and constitutes a puncturing portion capable of puncturing the wall of the organ. The elongated body distal end tip 43 has a truncated conical tip shape and the electrode 43a is formed so as to surround an elongated body distal end opening 4c formed in the upper end surface of the truncated cone. An electric potential is transmitted to the electrode 43a through a wire 44, but when the inner elongated body 41 or the outer tube 42 is a sheath of a conductive material, these members can be used as the wire 44. The electrode 43a illustrated in FIG. 2 is a monopolar type, but the electrode 43a of the elongated body distal end tip 43 may be a bipolar type.

Further, the elongated body distal end opening 4c illustrated in FIG. 2 communicates with the innermost lumen 41c of the inner elongated body 41. The guiding elongated body 4 can flush the contrast agent introduced into the innermost lumen 41c from the proximal end side of the inner elongated body 41 into the body from the elongated body distal end opening 4c.

As the inner elongated body 41 with the innermost lumen 41c or the outer tube 42, a coil tube formed by spirally winding a metal wire such as a stainless steel wire, a flexible metal pipe formed by cutting a metal pipe by laser beam processing or etching, a resin tube formed of PTFE or other resin, and the like can be used. Further, the elongated body distal end tip 43 can be formed by the electrode 43a, the wire 44, and resin covering them.

As illustrated in FIG. 1, the proximal end of the guiding elongated body 4 is exposed from the inner lumen 21c through the proximal end opening 21a of the inner sheath 21 and is connected to a slide operation unit 7. The slide operation unit 7 is an operation unit for changing the flexibility of the variable tip area (see FIG. 4) of the guiding elongated body 4. The operator operates a lever provided in the slide operation unit 7 so as to move the outer tube 42 and the inner elongated body 41 illustrated in FIGS. 2 and 4 in the axial direction. Accordingly, the flexibility of the variable tip area 45 can be easily and rapidly changed between a first state and a second state.

A wiring cord connected to a generator 8 supplying power to the wire 44 of the guiding elongated body 4 is connected to the slide operation unit 7 and an electric potential is transmitted from the proximal end of the guiding elongated body 4 to the electrode 43a provided in the distal end of the guiding elongated body 4.

FIG. 4A is a side view illustrating the second state of the variable tip area 45 of the guiding elongated body 4 and FIG. 4B is a side view illustrating the first state of the variable tip area 45. The guiding elongated body 4 includes the variable tip area 45 which is provided in the vicinity of the distal end of the guiding elongated body 4, and the variable tip area 45 has an ability of changing the flexibility by the operation of the slide operation unit 7 connected to the proximal end. In the guiding elongated body 4, when the outer tube 42 is pulled toward the proximal end side with respect to the fixed inner elongated body 41 as indicated by an arrow of FIG. 4B, the inner elongated body 41 is exposed from the distal end of the outer tube 42.

As illustrated in FIG. 4B, when the variable tip area 45 of the guiding elongated body 4 is in the first state, the inner elongated body 41 is exposed from the distal end of the outer tube 42 and the exposure length is a first length. As illustrated in FIG. 4B, the variable tip area 45 in the first state has predetermined flexibility. When the distal end of the guiding elongated body 4 contacts a wall of an organ 78, the variable tip area 45 is easily bent and the distal end of the guiding elongated body 4 moves along the wall of the organ 78. The flexibility of the variable tip area 45 in the first state is the same as the flexibility of the inner elongated body 41 alone exposed from the outer tube 42 and, for example, the flexibility of the inner elongated body 41 can be set to be substantially the same as that of the general guide wire.

As illustrated in FIG. 4A, when the variable tip area 45 of the guiding elongated body 4 is in the second state, the exposure length in which the inner elongated body 41 is exposed from the distal end of the outer tube 42 is a second length shorter than the first length in the first state. In this case, a state in which the exposure length is the second length includes a state in which the inner elongated body 41 is not exposed from the distal end of the outer tube 42 (a state in which the exposure length is 0). As illustrated in FIG. 4A, the variable tip area 45 in the second state is stiffer than the first state. Even when the distal end of the guiding elongated body 4 contacts a wall of an organ, the variable tip area 45 is not easily bent and the distal end of the guiding elongated body 4 can be pressed against the wall of the organ.

The flexibility of the variable tip area 45 in the second state is the same as the flexibility of the proximal end side portion in relation to the variable tip area 45 of the guiding elongated body 4 (a portion in which the outer tube 42 and the inner elongated body 41 with the innermost lumen 41c are double tubes). For example, the flexibility of the portion in which the outer tube 42 and the inner elongated body 41 are double tubes can be set to the flexibility lower than that of the general guide wire. Additionally, the distal end portion of the inner elongated body 41 is provided with a precurved bending and the bending is corrected by the rigidity of the outer tube 42 in the outer tube 42 so that the distal end portion of the inner elongated body 41 has a linear shape. When the distal end portion is exposed from the outer tube 42, the distal end portion of the inner elongated body 41 may be curved due to the bending.

Since the stent delivery device 1 including the guiding elongated body 4 changes the flexibility of the variable tip area 45 of the guiding elongated body 4 depending on the internal body condition in the vicinity of the distal end of the stent delivery device 1 or the procedure thereof, it is possible to shorten the time necessary for the procedure and to rapidly transport and indwell the stent 5 to the indwelling site.

Figure 8:
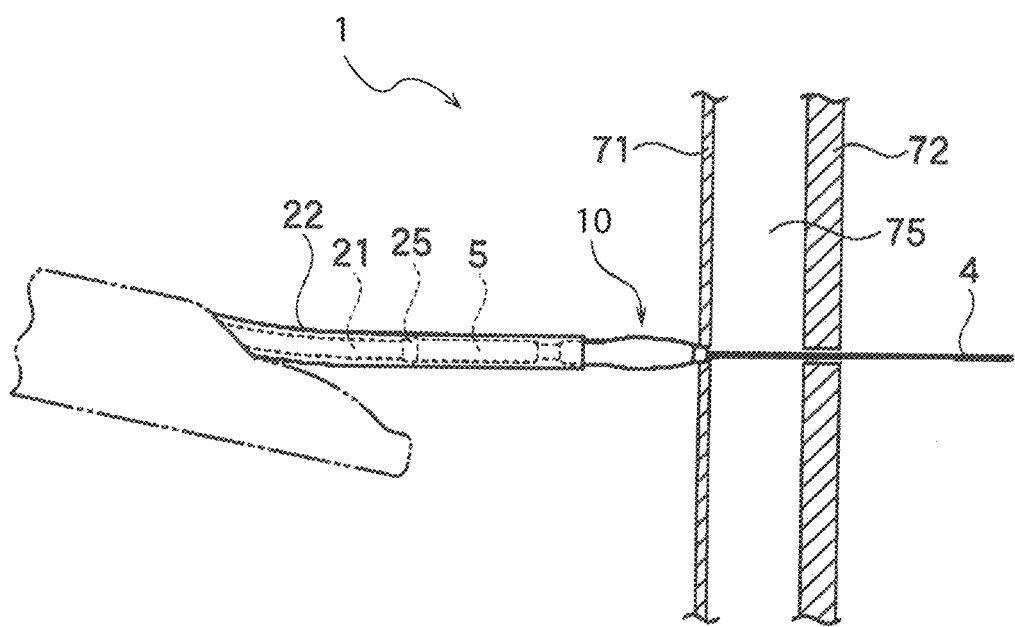
FIG. 8 is a diagram illustrating a puncturing operation using the stent delivery device illustrated in FIG. 1.

For example, FIG. 8 illustrates one procedure using the stent delivery device 1 and illustrates a procedure of puncturing a stomach wall 71 and a bile duct wall 72 interposing an abdominal cavity 75 therebetween. In the procedure illustrated in FIG. 8, first, as illustrated in FIG. 4A, when the guiding elongated body 4 is set to the second state, the electrode 43a (see FIG. 2) provided in the distal end of the guiding elongated body 4 is pressed against the stomach wall 71 and cauterizes and punctures the stomach wall 71. Further, when the guiding elongated body 4 is further pushed outward while the variable tip area 45 is maintained in the second state in which the variable tip area is stiffer and hardly bent, the guiding elongated body 4 penetrates the punctured hole of the stomach wall 71 so that the distal end of the guiding elongated body 4 reaches the bile duct wall 72. Further, when the bile duct wall 72 is also punctured similarly to the stomach wall 71 and the guiding elongated body 4 is pushed inward while the variable tip area 45 is maintained in the second state, the guiding elongated body 4 can be located inside a bile duct 76.

Figure 9:
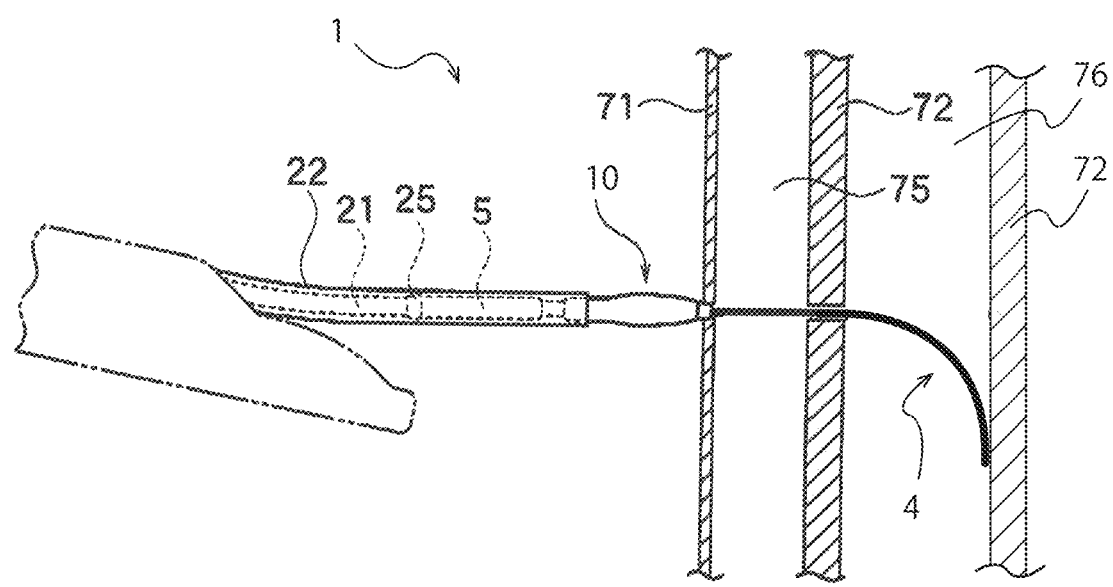
FIG. 9 is a diagram illustrating a catheter guiding operation using the stent delivery device illustrated in FIG. 1.

FIG. 9 is a diagram illustrating another procedure using the stent delivery device 1 and illustrating a procedure performed after the procedure illustrated in FIG. 8. In the procedure illustrated in FIG. 9, first, as illustrated in FIG. 4B, the guiding elongated body 4 is set to the first state. Then, when the guiding elongated body 4 is further inserted into the body after the guiding elongated body 4 is set to the first state, the distal end of the guiding elongated body 4 can be moved to the indwelling position of the stent 5 inside the bile duct 76 along the bile duct wall 72 (the inner wall). Subsequently, the catheter 2 is inserted into the bile duct 76 along the guiding elongated body 4 and the stent 5 can be transported and indwelled to the indwelling position.

In this way, in the stent delivery device 1, when the variable tip area 45 of the guiding elongated body 4 is set to the second state, the electrode 43a located at the distal end of the guiding elongated body 4 can be strongly pressed against the punctured site and hence the puncturing can be rapidly performed. Further, if the variable tip area 45 of the guiding elongated body 4 is set to the first state when the puncturing is not performed, it is possible to prevent the distal end of the guiding elongated body 4 from being strongly pressed against a wall of an organ, such as the bile duct wall 72 or the like. Further, since the guiding elongated body 4 has the function of a puncturing tool or dilator and the function of guiding the catheter 2 like a guide wire, it is possible to omit a replacement operation (a procedure) of a wire or the like inserted through the inner lumen 21c (see FIG. 1) of the catheter 2 and to rapidly transport the stent 5 to the indwelling position.

Second Embodiment

FIG. 5A is a side view illustrating a second state of a variable tip area 245 of a guiding elongated body 204 of a stent delivery device according to a second embodiment of the invention and FIG. 5B is a side view illustrating a first state of the variable tip area 245. The stent delivery device according to the second embodiment is different from the stent delivery device 1 according to the first embodiment in that an operation wire 206 operating the direction of the distal end of the guiding elongated body 204 is provided and a method of changing the flexibility of the variable tip area 245 is different. However, the stent delivery device according to the second embodiment is the same as the stent delivery device 1 according to the first embodiment except for these different points. Thus, in the description of the stent delivery device according to the second embodiment, only the different points of the stent delivery device 1 will be described and the description of the common points with the stent delivery device 1 will be omitted.

As illustrated in FIGS. 5A and 5B, the guiding elongated body 204 includes the inner elongated body 41, the outer tube 42 through which the inner elongated body 41 is slidably inserted, and the elongated body distal end tip 43 similarly to the guiding elongated body 4 illustrated in FIGS. 4A and 4B. However, in the guiding elongated body 204, when the inner elongated body 41 is pushed to the distal end side of the fixed outer tube 42 as indicated by an arrow of FIG. 5B, the inner elongated body 41 is exposed from the distal end of the outer tube 42.

The first state of the variable tip area 245 of the guiding elongated body 204 illustrated in FIG. 5B is the same as the first state of the variable tip area 45 of the guiding elongated body 4 illustrated in FIG. 4B and the second state of the variable tip area 245 of the guiding elongated body 204 illustrated in FIG. 5A is the same as the second state of the variable tip area 45 of the guiding elongated body 4 illustrated in FIG. 4A.

As illustrated in FIGS. 5A and 5B, the distal end of the operation wire 206 is connected to the elongated body distal end tip 43 of the guiding elongated body 204. The operation wire 206 is inserted through the inner lumen 21c of the inner sheath 21 of the catheter 2 (see FIG. 1) in parallel to the guiding elongated body 204. The proximal end of the operation wire 206 is exposed from the proximal end opening 21a of the inner sheath 21 to the outside and the operator of the stent delivery device can operate the bending and stretching of the distal end of the guiding elongated body 4 by operating the proximal end of the operation wire 206 in the axial direction.

The stent delivery device including such an operation wire 206 can rapidly transport the stent 5 to the indwelling site by rapidly performing a procedure in such a manner that the operator operates the bending and stretching in the vicinity of the distal end of the guiding elongated body 204. Further, the stent delivery device according to the second embodiment has the same effect as that of the stent delivery device according to the first embodiment.

Third Embodiment

FIG. 6A, is a side view illustrating a second state of a variable tip area 345 of a guiding elongated body 304 of a stent delivery device according to a third embodiment of the invention and FIG. 4j is a side view illustrating a first state of the variable tip area 345. The stent delivery device according to the third embodiment is the same as the stent delivery device 1 according to the first embodiment except that the structure of the distal end portion of the guiding elongated body 304 is different. Thus, in the description of the stent delivery device according to the third embodiment, only the different points from the stent delivery device 1 will be described and the description of the common points with the stent delivery device 1 will be omitted.

As illustrated in FIGS. 6A and 6B the guiding elongated body 304 includes an inner elongated body 341 which is a wire, an outer tube 342 through which the inner elongated body 341 is slidably inserted, and an elongated body distal end tip 343. The elongated body distal end tip 343 is different from the elongated body distal end tip 43 according to the first embodiment in that the elongated body distal end tip is connected to the outer tube 342, but is the same as the elongated body distal end tip 43 illustrated in FIG. 2 in that the elongated body distal end tip includes the electrode 43a.

As illustrated in FIG. 6B when the variable tip area 345 of the guiding elongated body 304 is in the first state, the distal end of the inner elongated body 341 is pressed to the proximal end side with respect to the distal end of the outer tube 342. Thus, when the variable tip area 345 of the guiding elongated body 304 is in the first state, a non-overlapping portion of the outer tube 342 and the inner elongated body 341 is formed in the vicinity of the distal end of the guiding elongated body 304 and a non-overlapping length corresponding to the length of that portion is a third length. The outer tube 342 includes a coiled portion 342a which is formed in a portion where the variable tip area 345 is located and which is formed as a coil tube formed of a metal wire so that a tube wall is spirally wound. The flexibility of the variable tip area 345 in the first state is the same as the flexibility of the coiled portion 342a alone in the outer tube 342 from which the inner elongated body 341 is pulled out.

As illustrated in FIG. 6A, when the variable tip area 345 of the guiding elongated body 304 is in the second state, a non-overlapping length in which the outer tube 342 does not overlap the inner elongated body 341 is a fourth length shorter than the third length in the first state. In this case, a state in which the non-overlapping length is the fourth length includes a state in which the inner elongated body 341 matches the distal end of the outer tube 342 (a state in which the non-overlapping length is 0). The variable tip area 345 corresponding to the second state illustrated in FIG. 6A is stiffer than the variable tip area 345 corresponding to the first state illustrated in FIG. 6B similarly to the variable tip area 45 of the guiding elongated body 4 described with reference to FIGS. 4A and 4B. Additionally, in the third embodiment of the invention, in order to allow the inner elongated body 341 to have rigidity as large as possible, the inner elongated body 341 is desirably a wire not including a lumen formed therein. For example, a wire formed of metal such as stainless steel can be used.

When the inner elongated body 341 is pulled toward the proximal end side with respect to the fixed outer tube 342 as indicated by an arrow of FIG. 6B, the variable tip area 345 of the guiding elongated body 304 changes from the second state illustrated in FIG. 6A to the first state illustrated in FIG. 6B. The stent delivery device according to the third embodiment with such a guiding elongated body 304 has the same effect as that of the stent delivery device 1 according to the first embodiment.

Fourth Embodiment

FIG. 7A is a side view illustrating a second state of a variable tip area 445 of a guiding elongated body 404 of a stent delivery device according to a fourth embodiment of the invention and FIG. 7B is a side view illustrating a first state of the variable tip area 445. The stent delivery device according to the fourth embodiment is the same as the stent delivery device 1 according to the first embodiment except that the structure of the distal end portion of the guiding elongated body 404 is different. Thus, in the description of the stent delivery device according to the fourth embodiment, only the different points from the stent delivery device 1 will be described and the description of the common points with the stent delivery device 1 will be omitted.

As illustrated in FIGS. 7A and 7B, the guiding elongated body 404 includes an inner elongated body 441, an outer tube 442 through which the inner elongated body 441 is slidably inserted, and an elongated body distal end tip 443. Since the elongated body distal end tip 443 is connected to both of the inner elongated body 441 and the outer tube 442, this elongated body distal end tip is different from the elongated body distal end tip 43 according to the first embodiment, but is the same as the elongated body distal end tip 43 illustrated in FIG. 2 in that the electrode 43a is provided.

As illustrated in FIGS. 7A and 7B, the outer tube 442 includes a telescopic distal end portion 442a provided in the vicinity of the distal end of the outer tube 442 and having elasticity in the axial direction while changing the flexibility. The telescopic distal end portion 442a is formed as a coil tube formed of a metal wire so that a tube wall is spirally wound.

As illustrated in FIG. 7B, when the variable tip area 445 of the guiding elongated body 404 is in the first state, the telescopic distal end portion 442a of the outer tube 442 is expanded in the axial direction. Accordingly, the flexibility of the telescopic distal end portion 442a is higher than that of the second state in which the telescopic distal end portion 442a is contracted.

In contrast, as illustrated in FIG. 7A, when the variable tip area 445 of the guiding elongated body 404 is in the second state, the telescopic distal end portion 442a of the outer tube 442 is contracted in the axial direction. Accordingly, the flexibility of the telescopic distal end portion 442a is lower than that of the first state in which the telescopic distal end portion 442a is expanded.

In the variable tip area 445 of the guiding elongated body 404, the flexibility of the outer tube 442 with the telescopic distal end portion 442a changes between the first state and the second state as described above and the flexibility of the inner elongated body 441 does not change. Thus, the variable tip area 445 in the second state illustrated in FIG. 7A is stiffer than the variable tip area 445 corresponding to the first state illustrated in FIG. 7B similarly to the variable tip area 45 of the guiding elongated body 4 described with reference to FIGS. 4A and 4B.

The variable tip area 445 of the guiding elongated body 404 changes from the second state illustrated in FIG. 7A to the first state illustrated in FIG. 7B when the inner elongated body 441 is pushed toward the distal end side while the proximal end of the outer tube 442 is fixed. The stent delivery device according to the fourth embodiment with such a guiding elongated body 404 has the same effect as that of the stent delivery device 1 according to the first embodiment.

Figure 3:
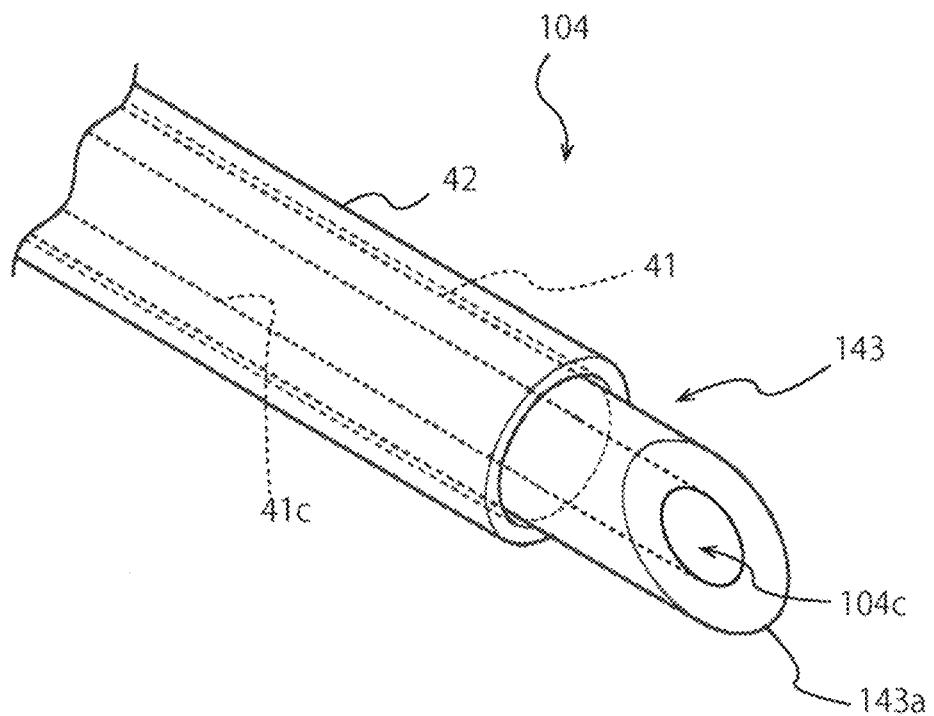
FIG. 3 is a perspective view illustrating a distal end portion of a guiding elongated body according to a modified example.

As described above, the invention has been described with reference to the embodiments, but the invention is not limited to the above-described embodiments. It is needless to mention that many other embodiments and modifications are included. For example, FIG. 3 is a perspective view illustrating the distal end portion of a guiding elongated body 104 according to the modified example. The guiding elongated body 104 is the same as the guiding elongated body 4 except that the elongated body distal end tip 143 is different from the elongated body distal end tip 43 of the guiding elongated body 4 illustrated in FIG. 2.

As illustrated in FIG. 3, the elongated body distal end tip 143 provided in the distal end of the guiding elongated body 104 includes a needle 143a capable of puncturing a wall of an organ while being pressed against the wall of the organ with a predetermined force. Such a guiding elongated body 104 can have a function of a puncturing tool and a function of guiding the catheter 2 by changing the flexibility of the variable tip of the guiding elongated body 104. Further, as the guiding elongated body of the stent delivery device of the invention, the invention is not limited to one having a puncturing portion provided at its distal end. For example, it may have a function other than puncturing, such as a dilator that expands a puncture hole or may have only a function of guiding a catheter.

FIG. 10A is a side view illustrating a second state of a variable tip area 545 of a guiding elongated body 504 of a stent delivery device according to a second modified example of the invention and FIG. 10B is a side view illustrating a first state of the variable tip area 545. The stent delivery device according to the second modified example is the same as the stent delivery device according to the third embodiment illustrated in FIGS. 6A and 6B except that the guiding elongated body 504 includes a covering tube 511. Thus, in the description of the stent delivery device according to the second modified example, only the different points from the stent delivery device according to the third embodiment will be described and the description of the common points with the stent delivery device according to the third embodiment will be omitted.

As illustrated in FIGS. 10A and 10B, the guiding elongated body 504 includes the covering tube 511 which covers the outer periphery of the distal end part of the guiding elongated body 504. The outer tube 342 and the inner elongated body 341 are inserted through the covering tube 511 and the elongated body distal end tip 343 provided in the distal end of the outer tube 342 is exposed from the distal end of the covering tube 511.

Since the covering tube 511 covers the outer periphery of the coiled portion 342a of the guiding elongated body 504, it is possible to prevent the coiled portion 342a from directly contacting a wall of an organ. For example, as illustrated in FIG. 10B, when the guiding elongated body 504 is in the first state, the coiled portion 342a is partially expanded and contracted to exhibit the flexibility. However, when the covering tube 511 covers the coiled portion 342a, it is possible to prevent a problem in which the expanded and contracted portion of the coiled portion 342a is caught by a wall of an organ. Further, since the covering tube 511 guides the bending of the coiled portion 342a, it is possible to prevent a force in the bending direction from being concentrated on only a part of the coiled portion 342a and to prevent the coiled portion 342a from being bent in a direction unexpected to the operator.

As the covering tube 511, for example, a resin tube having flexibility can be exemplified and the covering tube 511 can be formed of the same material as those of the inner sheath 21 and the outer sheath 22. Further, the stent delivery device including the guiding elongated body 504 illustrated in FIGS. 10A and 10B has the same effect as that of the stent delivery device according to the third embodiment.

EXPLANATIONS OF LETTERS OR NUMERALS

1 STENT DELIVERY DEVICE
2 CATHETER
21 INNER SHEATH
21a PROXIMAL END OPENING
21c INNER LUMEN
22 OUTER SHEATH
25 FIXING RING
3 OPERATION UNIT
31 RELEASE HANDLE
32 RELEASE LEVER
4, 104, 204, 304, 404, 504 GUIDING ELONGATED BODY
4c, 104c ELONGATED BODY DISTAL END OPENING
41, 341, 441 INNER ELONGATED BODY
41c INNERMOST LUMEN
42, 342, 442 OUTER TUBE
342a COILED PORTION
442a TELESCOPIC DISTAL END PORTION
43, 143, 343, 443 ELONGATED BODY DISTAL END TIP
43a ELECTRODE
143a NEEDLE
44 WIRE
45, 245, 345, 445, 545 VARIABLE TIP AREA
5 STENT
10 DISTAL END TIP
206 OPERATION WIRE
7 SLIDE OPERATION UNIT
8 GENERATOR
71 STOMACH WALL

72 BILE DUCT WALL
75 ABDOMINAL CAVITY
76 BILE DUCT
78 WALL OF ORGAN
511 COVERING TUBE

The invention claimed is:

1. A stent delivery device comprising:
a catheter including an inner sheath and an outer sheath allowing the inner sheath to be slidably inserted therethrough;
a stent provided between the inner sheath and the outer sheath in the vicinity of a distal end of the catheter; and
a guiding elongated body inserted through an inner lumen of the inner sheath and is partially capable of exposed from the distal end of the catheter so as to guide the insertion of the catheter,
wherein the guiding elongated body has a variable tip area provided in the vicinity of a distal end of the guiding elongated body, and the variable tip area has an ability of changing flexibility between a first state in which the variable tip area has predetermined flexibility and a second state in which the variable tip area is stiffer than the first state,
wherein the guiding elongated body includes a puncturing portion provided in the distal end of the guiding elongated body so as to puncture a wall of an organ, and
wherein the puncturing portion includes an electrode for cauterizing a wall of an organ.

2. The stent delivery device according to claim 1, wherein the guiding elongated body includes an inner elongated body and an outer tube through which the inner elongated body is slidably inserted.

3. The stent delivery device according to claim 2, wherein when the variable tip area is in the first state, an exposure length in which the inner elongated body is exposed from a distal end of the outer tube is a first length, and wherein when the variable tip area is in the second state, the exposure length is a second length shorter than the first length.

4. The stent delivery device according to claim 2, wherein when the variable tip area is in the first state, a non-overlapping length in which the outer tube and the inner elongated body do not overlap each other in the vicinity of the distal end of the guiding elongated body is a third length, and wherein when the variable tip area is in the second state, the non-overlapping length is a fourth length shorter than the third length.

5. The stent delivery device according to claim 2, wherein the outer tube includes a telescopic distal end portion which is provided in the vicinity of a distal end of the outer tube and having elasticity in an axial direction while changing the flexibility.

6. The stent delivery device according to claim 1, further comprising:
an operation wire connected to the distal end of the guiding elongated body and inserted through the inner lumen of the inner sheath in parallel to the guiding elongated body,
wherein the operation wire is used to operate bending and stretching in the vicinity of the distal end of the guiding elongated body.

7. The stent delivery device according to claim 2, further comprising:
an operation wire connected to the distal end of the guiding elongated body and inserted through the inner lumen of the inner sheath in parallel to the guiding elongated body,
wherein the operation wire is used to operate bending and stretching in the vicinity of the distal end of the guiding elongated body.

8. The stent delivery device according to claim 3, further comprising:
an operation wire connected to the distal end of the guiding elongated body and inserted through the inner lumen of the inner sheath in parallel to the guiding elongated body,
wherein the operation wire is used to operate bending and stretching in the vicinity of the distal end of the guiding elongated body.

9. The stent delivery device according to claim 4, further comprising:
an operation wire connected to the distal end of the guiding elongated body and inserted through the inner lumen of the inner sheath in parallel to the guiding elongated body,
wherein the operation wire is used to operate bending and stretching in the vicinity of the distal end of the guiding elongated body.

10. The stent delivery device according to claim 5, further comprising:
an operation wire connected to the distal end of the guiding elongated body and inserted through the inner lumen of the inner sheath in parallel to the guiding elongated body,
wherein the operation wire is used to operate bending and stretching in the vicinity of the distal end of the guiding elongated body.

* * * * *